(12) United States Patent
Warnecke et al.

(10) Patent No.: US 8,609,860 B2
(45) Date of Patent: Dec. 17, 2013

(54) ACID-LABILE TRIGGER UNITS

(75) Inventors: André Warnecke, Freiburg (DE);
Ivonne Müller, Einbeck (DE)

(73) Assignee: KTB Tumorforschungsgesellschaft mbH, Freiburg Im Breisgau (DE)

( * ) Notice: Subject to any disclaimer, the term of this patent is extended or adjusted under 35 U.S.C. 154(b) by 143 days.

(21) Appl. No.: 13/379,131

(22) PCT Filed: Jun. 21, 2010

(86) PCT No.: PCT/EP2010/003732
§ 371 (c)(1),
(2), (4) Date: Feb. 23, 2012

(87) PCT Pub. No.: WO2010/149326
PCT Pub. Date: Dec. 29, 2010

(65) Prior Publication Data
US 2012/0142711 A1    Jun. 7, 2012

(30) Foreign Application Priority Data
Jun. 22, 2009  (EP) .................................... 09008150

(51) Int. Cl.
*C07D 403/12* (2006.01)
*C07D 405/12* (2006.01)
*C07D 473/00* (2006.01)
*C07D 491/22* (2006.01)
*A61K 31/4192* (2006.01)
*A61K 31/513* (2006.01)
*A61K 31/52* (2006.01)

(52) U.S. Cl.
USPC ............ 548/256; 548/255; 546/48; 544/265; 544/310; 514/263.2; 514/274; 514/283; 514/359

(58) Field of Classification Search
USPC ............ 548/255, 256; 546/48; 544/265, 310; 514/263.2, 274, 283, 359
See application file for complete search history.

(56) References Cited

PUBLICATIONS

De Groot, Franciscus M.H., et al., "Synthesis and Biological Evaluation of Novel Prodrugs of Anthracyclines for Selective Activation by the Tumor-Associated Protease Plasmin," J. Med. Chem., 1999, vol. 42, pp. 5277-5283.
Gopin, Anna, et al., "New Chemical Adaptor Unit Designed to Release a Drug From a Tumor Targeting Device by Enzymatic Triggering," Bioorganic & Medicinal Chemistry, 2004, vol. 12, pp. 1853-1858.
Kratz, Felix, et al., "Prodrug Strategies in Anticancer Chemotherapy," ChemMedChem, 2008, vol. 3, pp. 20-53.
Shabat, Doron, et al., "Chemical Adaptor Systems," Chem. Eur. J., 2004, vol. 10, pp. 2626-2634.

*Primary Examiner* — Shailendra Kumar
(74) *Attorney, Agent, or Firm* — McDonnell Boehnen Hulbert & Berghoff LLP

(57) ABSTRACT

The present invention relates to a compound comprising an imine bond as an acid-labile trigger group, the use of such an imine bond as an acid-labile trigger group, a process of cleaving the imine bond in said compound, and a pharmaceutical composition comprising said compound.

13 Claims, 6 Drawing Sheets

ACID-LABILE TRIGGER UNITS

This application is a U.S. national phase of International Application No. PCT/EP2010/003732, filed Jun. 21, 2010, which claims priority to a corresponding patent application filed in Europe and having application number EP 09008150.6, filed Jun. 22, 2009, the entire contents of which are herein incorporated by reference.

The present invention relates to a compound comprising an imine bond as an acid-labile trigger group, the use of such an imine bond as an acid-labile trigger group, a process of cleaving the imine bond in said compound, and a pharmaceutical composition comprising said compound.

Most of the drugs used at present are small molecules, i.e., compounds with low molecular weights and exhibit, when systemically administered to a patient, a high plasma clearance. Furthermore, said low molecular weight compounds show a high tendency to penetrate body tissues by diffusion, resulting in a uniform biodistribution. These are the two main reasons why only small quantities of the drug reach the site of action and, due to distribution over healthy tissues of the body, said drugs might give rise to problematic side-effects. These disadvantages are of particular concern for those drugs having a high cytotoxic potential, such as cytotoxic agents, immuno-suppressive agents or virostatic agents.

Especially for the treatment of cancer several strategies have been pursued for improving the selectivity of low molecular weight drugs and thus to increase the concentration of the active agent in the desired tissue, while the concentration of the same is decreased in healthy tissues in order to reduce side-effects. In this context, the prodrug approach has been developed according to which the drug is administered to an organism in an inactive or less active form and is converted, e.g. by metabolization, into the active form. Prodrugs can also be generated by conjugating the respective drug with a suitable carrier.

For example, macromolecules, such as antibodies, peptides or synthetic polymers, have been investigated as drug carriers for the development of prodrugs, since such macromolecules accumulate in tumor tissues (Kratz, F.; Müller, I. A.; Ryppa, C.; Warnecke, A. *ChemMedChem* 2008, 3, 20-53; R. Duncan, *Nat. Rev. Drug Discovery* 2003, 347-360).

In such prodrugs, the drug is covalently bound to a macromolecular carrier via a suitable cross-linker. Incorporation of a pre-determined breaking point into said linker group allows the drug to be released in malignant tissue upon site-specific cleavage (cf. FIG. 1a). When administered parenterally, the linker should fulfill certain prerequisites, i.e., a high stability in the infusion solution, in the bloodstream as well as in tissue fluids of healthy tissue. Moreover, such linker groups should be cleaved effectively and selectively in tumor tissue after cellular uptake by the tumor cell exploiting the specific biochemical and/or pathophysiological characteristics of the target tissue and the target cells. In a related prodrug approach, the drug is covalently bound to a macromolecular carrier via an adapter unit (Shabat, D.; Amir, R. J.; Gopin, A.; Pessah, N.; Shamis, M. Chemical adaptor systems. *Chemistry Eur. J.* 2004, 10, 2626-2634). Said adapter unit is a self-immolative linker which disassembles upon activation of a trigger group being connected to the adapter unit (cf. FIG. 1b). Said trigger group should fulfill the same prerequisites as the above linker, namely a high stability in the infusion solution, in the bloodstream as well as in tissue fluids of healthy tissue. Moreover, such trigger group should be activated effectively and selectively in tumor tissue, thus leading to the disassembling of the adaptor unit and to a release of the drug. Compared to the prodrug approach depicted in FIG. 1a, the prodrug approach with an adapter unit (cf. FIG. 1b) is more versatile since the incorporation of an additional self-immolative linker reduces the influence of the drug on the cleavage of the trigger group. Furthermore, the adapter can be adapted to the accessible functional groups of the respective drug, i.e., the adapter can be used to build a transient chemical linkage between two molecules, namely the drug and the trigger group, for which a direct linkage might be impossible for chemical reasons.

Several strategies for the realization of a site-specific activation of macromolecular prodrugs have been pursued such as enzymatic cleavage by disease-related proteases or reductive or pH-dependent cleavage. The latter exploits the differences of the pH value between the bloodstream, the cytosol and after intracellular uptake for a selective release of drugs.

In contrast to low-molecular weight compounds, the cellular uptake of macromolecules occurs not via diffusion through the cell membrane, but via endocytosis. During this process, the pH value decreases from initially 7.2-7.4 to about 6.5-5.0 in the endosomes. A subsequent conversion into primary or secondary lysosomes may even lead to a pH value of around 4. Moreover, it has been shown that the interstitial pH value in tumor tissue is generally 0.5-1.0 pH units lower compared to the respective pH value in healthy tissue. However, the cytosolic pH value of tumor cells generally does not differ from the pH value of other cells. Accordingly, said significant change in the pH value after cellular uptake in tumor tissue has been used to develop acid-labile bonds between the carrier and the drug. Examples for known acid-labile pre-determined breaking points are acetal bonds, cis-aconityl and trityl groups, and acyl hydrazones, and are described e.g. in F. Kratz, U. Beyer, M. T. Schütte, *Crit. Rev. Ther. Drug Carrier Sys.* 1999, 16, 245-288.

Prodrugs comprising acid-labile trigger groups provide the advantage that they can be used in a wide range of applications, since the decrease in the pH value is a characteristic feature of tumor tissue. To the contrary, prodrugs comprising trigger groups which are cleaved upon enzymatic activation can only be applied when there is an (over)expression of the target enzyme in the tumor entity to be treated.

The most commonly used acid-labile groups are acyl hydrazones. Specific acyl hydrazones have been developed that show significant differences between their stability at a pH 7 ($t_{1/2} >> 48$ h) and their stability at a pH 5 ($t_{1/2} < 30$ h), which is advantageous in view of their cleavage in tumor cells upon a decrease in the pH value. However, in order to couple a drug to a macromolecular carrier via an acid-labile hydrazone bond, it is necessary that the drug comprises either a carbonyl functionality or an acyl hydrazide group. Whereas cytostatic agents comprising an acyl hydrazide group are very rare, the keto-functionalized anthracyclines daunorubicin and doxorubicin have been used for the development of macromolecular prodrugs. One example is the acid-labile albumin-binding doxorubicin derivative DOXO-EMCH (INNO-206). However, this technique is not applicable to the majority of cytotoxic drugs which comprise hydroxy and/or amino moieties as the only reactive groups.

Therefore, the technical problem underlying the present invention is to provide a compound comprising an acid-labile trigger group which is suitably used as a prodrug, which has a high stability in the infusion solution, in the bloodstream and in the tissue fluid of healthy tissue, and which is cleaved effectively and selectively in tumor tissue after cellular uptake by the tumor, and which can be used in combination with a great variety of drugs, without the need of the presence of a carbonyl functionality or an acyl hydrazide group in the drug.

According to the present invention, the above technical problem is solved by providing a compound of the following general formula (I):

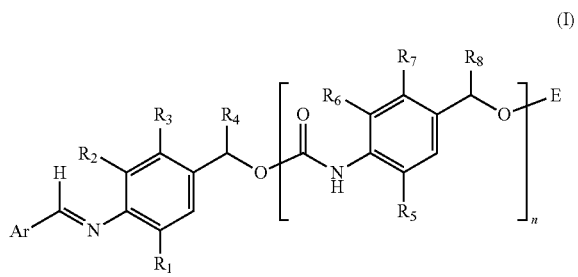

wherein
Ar is a phenyl group having one or more hydrogens substituted with a substituent independently selected from the group consisting of an $C_{1-6}$ alkyl group, a $C_{1-6}$ thioalkyl group, a $C_{3-7}$ cycloalkyl group which may contain one or more heteroatoms, an $C_{1-6}$ alkoxy group, a $C_{1-6}$ dialkylamine group, an $C_{1-6}$ alkoxycarbonyl group, a $C_{1-6}$ trialkylammonium group, a nitro group, a hydroxy group, a $C_{1-6}$ perfluoroalkyl group, fluorine, chlorine and bromine,
n is 0 or 1,
$R_1$, $R_2$, $R_5$ and $R_6$ are independently selected from hydrogen, a linear or branched $C_{1-8}$ alkyl group, a phenyl group, a naphthyl group, a biphenyl group or a vinyl benzene group, or a group C,
$R_3$, $R_4$, $R_7$ and $R_8$ are independently selected from hydrogen or a group C, with the proviso that not more than one of $R_1$ to $R_8$ is a group C,
E is a moiety comprising at least one effector unit selected from the group consisting of a dye, a diagnostic agent or a pharmaceutically active compound, and
C is a carrier group selected from the group consisting of serum proteins, antibodies or antibody fragments, synthetic polymers, dendrimers, peptides, growth factors, receptor-binding ligands, polysaccharids, microparticles, nanoparticles and protein-binding moieties capable of binding to a carrier molecule,
wherein the carrier group may be bound to the phenyl ring or to the benzylic carbon atom directly or via a linker.

In particular, the present invention relates to a compound which comprises an aryl imine unit as an essential structural feature. Said imine bond is acid-labile and can be hydrolyzed upon a reduction of the pH value. The pH value at which the imine bond is hydrolyzed, depends basically on the substituents of the aryl ring and can be selected appropriately. Moreover, the compound of the present invention further contains a benzyl alcohol-derived linker unit which is bound to the nitrogen atom of the aryl imine unit, and, optionally (i.e. when n is 1), a further linker unit. It has now surprisingly been found that upon activation of the trigger unit (i.e. when the imine bond of the aryl imine is hydrolyzed), the linker units disassemble by 1,6-benzyl elimination reactions and release the moiety E comprising at least one effector. These elimination reactions are exemplarily shown in FIG. 2 (for the case that n is 0). Accordingly, a new trigger system on the basis of an aryl imine has been developed, which may initiate the disassembling of a linker or adapter unit being based on the structure of p-aminobenzyl alcohol, thus leading to a release of a moiety E comprising at least one effector.

In the above formula (I), the group Ar is a phenyl group having one or more hydrogens substituted with a substituent independently selected from the group consisting of an $C_{1-6}$ alkyl group, a $C_{1-6}$ thioalkyl group, a $C_{3-7}$ cycloalkyl group which may contain one or more heteroatoms, an $C_{1-6}$ alkoxy group, a $C_{1-6}$ dialkylamine group, an $C_{1-6}$ alkoxycarbonyl group, a $C_{1-6}$ trialkylammonium group, a nitro group, a hydroxy group, a $C_{1-6}$ perfluoroalkyl group, fluorine, chlorine and bromine. The group Ar contains at least one substituent, i.e. at least one of the hydrogens of the phenyl ring is substituted by a substituent different from hydrogen. In a preferred embodiment of the present invention, the phenyl ring contains two or more substituents, in a more preferred embodiment of the present invention, the phenyl ring of the group Ar contains three, four or five substituents. The group Ar may contain electron-donating substituents and/or electron-withdrawing substituents. Preferred alkyl groups are methyl, ethyl, iso-propyl and tert-butyl. Preferred thioalkyl groups are thiomethyl, thioethyl, thio-iso-propyl and thio-tert-butyl. Preferred cycloalkyl groups are cyclopentyl and cyclohexyl. Preferred alkoxy groups are methoxy, ethoxy, iso-propoxy and tert-butoxy. Preferred dialkylamine groups are dimethylamine, diethylamine, di-iso-propylamine, dibutylamine, di-tert-butylamine and dihexylamine. Preferred alkoxycarbonyl groups are methoxycarbonyl, ethoxycarbonyl, iso-propoxycarbonyl and tert-butoxycarbonyl. Preferred trialkylammonium groups are trimethylammonium and triethylammonium. Preferred perfluoroalkyl groups are trifluoromethyl, pentafluoroethyl and heptafluoropropyl. It is further preferred that the group Ar contains one or more halogen atoms as substituents. These halogen atoms may be the same or different.

In a particularly preferred embodiment of the present invention, Ar is selected from one of the following groups:

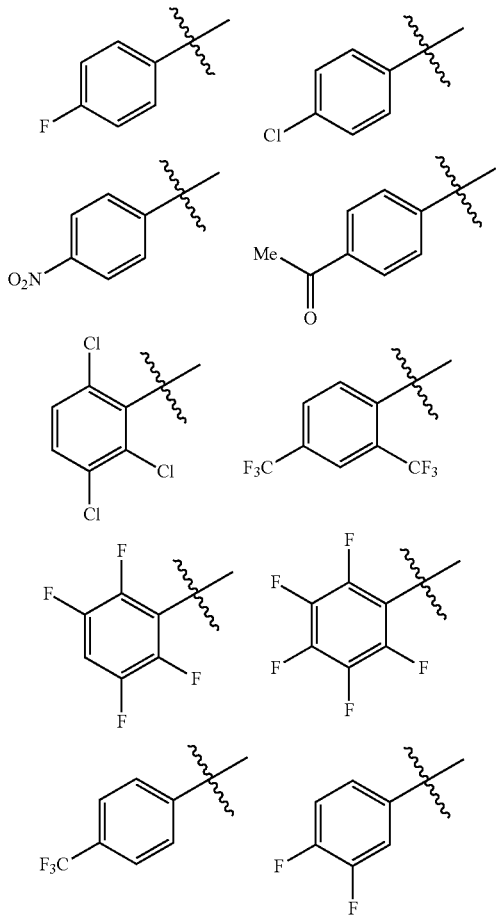

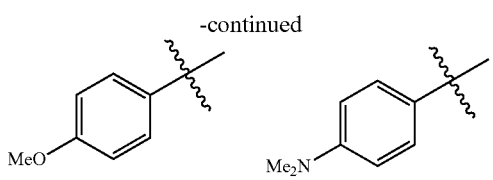

The above groups Ar are preferably used in the compound of the present invention, since it has been surprisingly found that aryl imines comprising the above aryl groups show a high stability under physiological conditions, i.e. at a pH value of about 7.4, and are easily hydrolyzed at lower pH values in the range of from about 3.5 to 5.5.

According to the present invention, the stability of the compounds of the present application refers to the stability in aqueous buffer solutions at pH 5 (acetate buffer) and pH 7.4 (phosphate buffer). Half-lives of imine hydrolysis are determined by measuring the decrease of the concentration of the imine and/or the increase of the concentration of the hydrolysis products e.g. by fluorescence methods, HPLC, infrared spectroscopy and/or NMR spectroscopy. In a preferred embodiment, the compounds of the present invention have half-lives of at least 20 hours at a pH of 7.4, more preferred of at least 80 hours at a pH of 7.4, and even more preferred of at least 300 hours at a pH of 7.4. In another preferred embodiment, the ratio of the half-lives at a pH of 7.4 to the half-lives at a pH of 5.0 ($t_{1/2}$(pH 7.4)/$t_{1/2}$(pH 5)) is at least 50, more preferred at least 100, and even more preferred at least 150.

For example, in the case of compounds comprising above groups Ar and the fluorescent dye AMC (cf. FIG. 3), half-lives of imine hydrolysis are determined by measuring the increase in fluorescence that corresponds to the release of AMC from the model compounds.

In a preferred embodiment of the present invention, Ar only contains electron-withdrawing substituents, since such substituents are capable of further enhancing the stability of the compound of the present invention under physiological conditions, i.e. at a pH value of about 7.4. Therefore, Ar is preferably selected from one of the following groups:

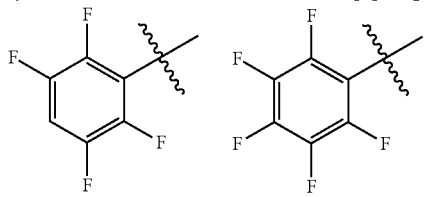

The compound of the present invention further comprises a linker unit having the following structure:

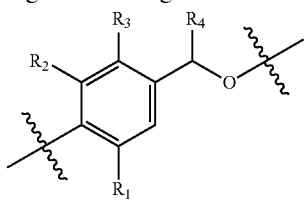

The compound of the present invention may further comprise another linker unit having the following structure:

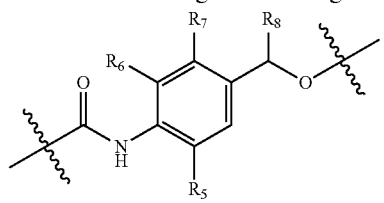

The presence of the latter linker group is indicated by the index n which may be 0 or 1. When n is 0, the above linker group is not present in the compound of the present invention. When n is 1, the above linker group is present in the compound of the present invention.

Upon activation of the aryl imine (i.e. the hydrolysis of the imine bond), the above linker groups disassemble via a 1,6-benzyl elimination. As a result, the group E is released.

$R_1$, $R_2$, $R_5$ and $R_6$ are independently selected from hydrogen, a linear or branched $C_{1-8}$ alkyl group, a phenyl group, a naphthyl group, a biphenyl group or a vinyl benzene group, or a group C. Moreover, $R_3$, $R_4$, $R_7$ and $R_8$ are independently selected from hydrogen or a group C. Preferred alkyl groups are methyl, ethyl, isopropyl and tert-butyl. The phenyl group, the naphthyl group and the biphenyl group may also contain one or more heteroatoms. However, in the compound of the present invention, not more than one of $R_1$ to $R_8$ is a group C.

Accordingly, the above linker groups may contain substituents selected from alkyl groups, a phenyl group, a naphthyl group, a biphenyl group or a vinyl benzene group. This is advantageous in view of further adjusting the stability of the imine bond of the adjacent aryl imine. For example, by including sterically demanding substituents at the positions $R_1$ and $R_2$, it is possible to provide a sterical hindrance at the imine bond leading to a decelerated hydrolysis of the imine bond and thus to a higher stability of the compound of the present invention under physiological conditions. Moreover, by including sterically demanding substituents at the positions $R_5$ and $R_6$, it is further possible to influence the rate of the elimination reaction leading to a decelerated disassembling of the linker units.

The above linker groups may also include a carrier group C. The incorporation of a carrier group C into the compound of the present invention is particularly advantageous in view of its application as a macromolecular prodrug. Accordingly, when a carrier group C is included in the above compound, the present invention makes use of the prodrug concept shown in FIG. 1b. In particular, when being used as a macromolecular prodrug, the effector (for example the pharmaceutically active compound) is generally transported to the desired site of action by means of an appropriate carrier. When using the compound of the present invention for therapeutic strategies against various diseases, it is especially preferred that the carrier group C is selected from targeting moieties such as antibodies or receptor-binding ligands or from macromolecules with inherent targeting properties, e.g. for passively targeting solid tumors (Kratz, F.; Müller, I. A.; Ryppa, C.; Warnecke, A. ChemMedChem 2008, 3, 20-53).

Accordingly, the carrier group C is selected from the group consisting of serum proteins, antibodies or antibody fragments, synthetic polymers, dendrimers, peptides, growth factors, receptor-binding ligands, polysaccharides, microparticles, nanoparticles and protein-binding moieties capable of binding to a carrier molecule. Suitable serum proteins are for example human serum transferrin and serum albumin. Suitable synthetic polymers are for example poly(ethylene glycols) (PEGs), monomethoxy PEG (mPEG), polyglycerol (PG), poly(ethylene imine) (PEI) and N-(2-hydroxypropyl)methacrylamide (HPMA) copolymers. These synthetic polymers may have a mass e.g. ranging from 2,000 to 200,000 Da. It is particularly preferable to use PEG having a mass ranging from 5,000 to 50,000 Da.

According to the present invention, only one of the groups $R_1$ to $R_8$ of the linker units may be the carrier group C, since it is desirable for sterical and synthetic reasons that the compound of the formula (I) does not contain more than one carrier group. Preferably, one of $R_2$, $R_3$, $R_4$, $R_6$, $R_7$ and $R_8$ is the carrier group C. It is particularly preferable that one of $R_3$ and $R_7$ is the carrier group. However, according to the present invention, it is not excluded that the compound of the formula (I) contains a carrier group C at a position different from the above groups $R_1$ to $R_8$. In particular, in one embodiment of the present invention, the compound of formula (I) contains a carrier group C as part of the moiety E. This carrier group C may be present in addition to a carrier group C at one of the positions $R_1$ to $R_8$, or instead of a carrier group at one of the positions $R_1$ to $R_8$.

In one preferred embodiment of the present invention, one of the substituents $R_1$ to $R_8$ is a carrier group C. In this case, it is preferred that the other substituents of $R_1$ to $R_8$ are hydrogen. In another preferred embodiment of the present invention, each of $R_1$ to $R_8$ is hydrogen, and the compound of the formula (I) contains a carrier group C within the moiety E. In another preferred embodiment of the present invention, each of $R_1$ to $R_8$ is hydrogen, and the compound of the formula (I) does not contain a carrier group C within the moiety E.

The carrier group may be bound to the phenyl ring (when $R_1$ to $R_3$ or $R_5$ to $R_7$ is the carrier group C) or to the benzylic carbon atom (when $R_4$ or $R_8$ is the carrier group C) directly or via a linker. The incorporation of a linker might become necessary for synthetic or steric reasons. Accordingly, the carrier group C may contain suitable functional groups such as hydroxy, amino or thiol groups to bind to the compound of the present invention. If necessary, these groups can be introduced in the carrier molecule by chemical modification through techniques known to those skilled in the art (Kratz et al., (2001): Anticancer drug conjugates with macromolecular carriers, in Polymeric Biomaterials, second edition, S. Dumitriu, Marcel Dekker, New York, Chapter 32, 851-894). For example, PEG may be coupled in its azide-functionalized form (PEG-$N_3$) to a ethynyl group via e.g. a copper-catalyzed Huisgen cycloaddition.

In a preferred embodiment of the present invention, one of $R_1$ to $R_8$ is a carrier group C and is a protein-binding moiety selected from the group consisting of a maleimide group, a halogenacetamide group, a halogenacetate group, a pyridylthio group, a vinylcarbonyl group, an aziridin group, a disulfide group, a substituted or unsubstituted acetylene group, and a hydroxysuccinimide ester group. In a further preferred embodiment of the present invention, one of $R_1$ to $R_8$ is a carrier group C and is a protein-binding moiety capable of in situ binding to cysteine-34 of serum albumin.

In another preferred embodiment of the present invention, one of $R_1$ to $R_8$ is a carrier group C and is a synthetic polymer selected from the group consisting of poly(ethylene glycol) (PEG), monomethoxy PEG (mPEG), polyglycerol (PG), poly(ethylene amine) (PEI) and N-(2-hydroxy)propylmethacrylamide (HPMA) copolymers. The use of PEG as the carrier is particularly preferable, since PEG conjugates can be easily purified by recrystallization. Moreover, the introduction of PEG enhances the solubility of hydrophobic groups (such as the trigger group and/or the effector units) in aqueous systems. Furthermore, PEG is chemically inert and is not UV-active. Accordingly, it is possible to detect UV-active effector units in the compound of the present invention e.g. by HPLC without an interference with the carrier group. In a preferred embodiment, one of $R_2$, $R_3$, $R_4$, $R_6$, $R_7$ and $R_8$ is the carrier group C, which is bound to the phenyl ring via a linker having one of the following structures, wherein m is an integer from 0 to 5:

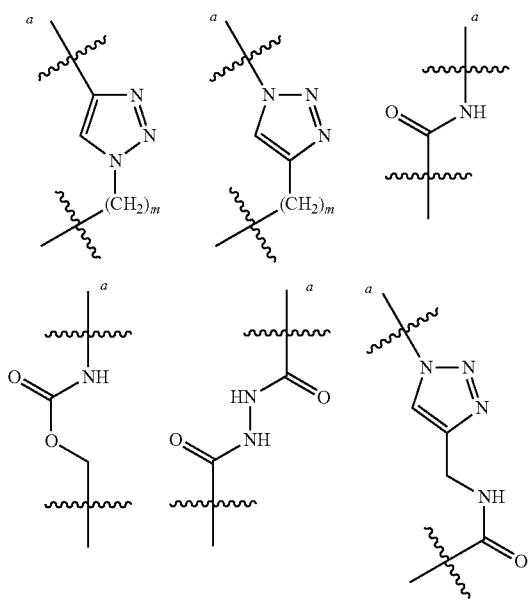

In the above linkers, the carrier is preferably bound at the position indicted as "a".

The compound of formula (I) according to the present invention further comprises a moiety E. Said moiety E is released upon hydrolysis of the imine bond and subsequent disassembling of the linker group(s). The moiety E contains at least one effector unit selected from the group consisting of a dye, a diagnostic agent or a pharmaceutically active compound. Besides that, there are no restrictions for the moiety E which can represent any suitable structural unit comprising a dye, a diagnostic agent or a pharmaceutically active compound. It is also possible that the moiety E contains more than one effector units which may be different or the same.

For example, the moiety E can be a dye or a pharmaceutically active compound which is directly bound to the benzylic oxygen of the linker group of the compound of formula (I).

It is also possible that the dye or the pharmaceutically active compound represents only a part of the moiety E. In a preferred embodiment of the present invention, the moiety E is a dendritic or linear system adapted to release one or more effector units upon cleavage of the imine bond in the compound of the formula (I). For example, the moiety E can be a self-immolative dendrimer. Such self-immolative dendrimers have been developed as prodrugs (reviewed in: Shabat, D. *J. Polym. Sci., Polym. Chem.* 2006, 44, 1569-1578; D. V. McGrath, *Mol. Pharm.* 2005, 2, 253-263) and are designed for a controlled and multiple release of small molecules. Based on self-eliminating linkers as branching units, self immolative dendrimers can be terminally loaded with various effector and/or reporter molecules. Activation at the focal point (namely hydrolysis of the imine bond of compound (I)) initiates a cascade of elimination reactions which lead to a breakdown of the whole dendritic scaffold with a concomitant release of several effector units. Alternatively, the moiety E can be a linear self-eliminating system which is based on branched self-eliminating linkers as monomer units. Upon activation by means of hydrolysis of the imine bond, the molecule disassembles in two directions, i.e. the bonds between two linkers that form the linear backbone as well as the bonds between the linker units and the effector molecules are cleaved by elimination reactions (cf. for example A. Warnecke, F. Kratz, *J. Org. Chem.* 2008, 73, 1546-1552).

Accordingly, the present invention includes for example the case where an effector unit is directly bound to the rest of the compound of formula (I). Moreover, the present invention includes also the case where several effector units are included e.g. in a linear self-eliminating or a dendritic system. According to the present invention, it is preferred that in all cases, the effector units are released upon hydrolysis of the imine bond.

According to a preferred embodiment of the present invention, the moiety E comprises at least one effector unit which is independently selected from the group consisting of a cytostatic agent, a cytokine, an immunosuppressant, an antirheumatic, an antiphlogistic, an antibiotic, an analgetic, a virostatic, an antimycotic agent, a transcription factor inhibitor, a cell cycle modulator, a MDR modulator, a vascular disrupting agent, a proteasome or protease inhibitor, an apoptosis modulator, an enzyme inhibitor, an angiogenesis inhibitor, a hormone or hormone derivative, a radioactive substance, a light emitting substance, or a light absorbing substance. It is particularly preferred that the moiety E comprises at least one cytostatic agent as an effector unit which is selected from the group consisting of N-nitrosoureas, the anthracyclines doxorubicin, daunorubicin, epirubicin, idarubicin, 2-(4-diacetoxybutyl)doxorubicin; the anthraquinones mitoxantrone and ametantrone; the alkylating agents chlorambucil, bendamustine, melphalan, and oxazaphosphorines; the antimetabolites 5-fluorouracil, 2'-deoxy-5-fluorouridine, cytarabine, cladribine, fludarabine, pentostatine, gemcitabine, 6-thioguanine and 6-mercaptopurine; the folic acid antagonists methotrexate, raltitrexed, pemetrexed and plevitrexed, the taxanes paclitaxel and docetaxel; the camptothecins topotecan, irinotecan (CPT-11), SN-38, 10-hydroxycamptothecin, GG211, lurtotecan, 9-aminocamptothecin and camptothecin; the lignans etoposide and podophyllotoxin; the Vinca alkaloids vinblastine, vincristine, vindesine and vinorelbine; calicheamicins; maytansinoids; auristatins; epothilones; tubulysins, rapamycin, salinosporamide, combretastatin, bleomycin; dactinomycin; plicamycin; mitomycin C and cis-configured platinum(II) complexes.

The effector unit can be directly bound to the rest of the moiety E or to the linker group of the compound of the formula (I). However, for synthetic reasons, it might be advantageous that the effector unit is not directly bound, but via a suitable linker group. Accordingly, it is preferred that the effector unit E is bound via a —C(O)O—, a —C(O)S—, a —C(O)NH—, a —CH$_2$O— or a —C(O)NH—CH$_2$N— group.

In the following, compounds according to the present invention which do not include a carrier group C are discussed.

In particular, in a preferred embodiment of the present invention, the compound of formula (I) has the following general formula (II):

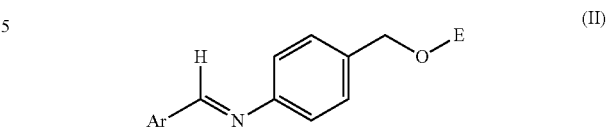

In the above formula (II), n is 0 and each of R$_1$ to R$_4$ is hydrogen. It is particularly preferable that the moiety E comprises the dye 7-amino-4-methylcoumarin (AMC) which is bound to the benzylic oxygen atom via a —C(O)NH— linker group. Said compound is represented by the following general formula (IX):

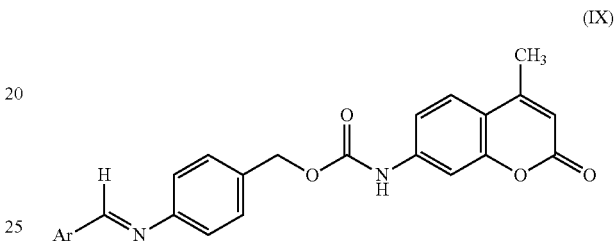

The compound of the above formula (IX) can be synthesized by the reaction scheme shown in FIG. 4. In particular, in a first step, the benzaldehyde of the respective aryl compound is reacted with p-aminobenzyl alcohol (PABA). Then, the resulting imine is reacted with the isocyanate derivative of the dye. Substituted benzaldehydes are readily available and the synthesis of the respective isocyanate derivatives is within the knowledge of a person skilled in the art. The use of the fluorophore AMC has the advantage that upon excitation at 390 nm, blue light with a wavelength of 460 nm is emitted. As long as the amino group is acetylated, the fluorescence of AMC is significantly decreased. Accordingly, the release of the dye can easily be detected e.g. by means of a fluorescence plate reader. Therefore, the release properties of the compounds of the present invention can be studied extremely well using AMC as a model.

In the following, compounds according to the present invention which include a carrier group C are described. In particular, in another preferred embodiment of the present invention, the compound of the present invention has one of the following structures (III), (IV), (V), (VI), (VII) or (VIII), wherein PEG is poly(ethylene glycol) or monomethoxy poly (ethylene glycol):

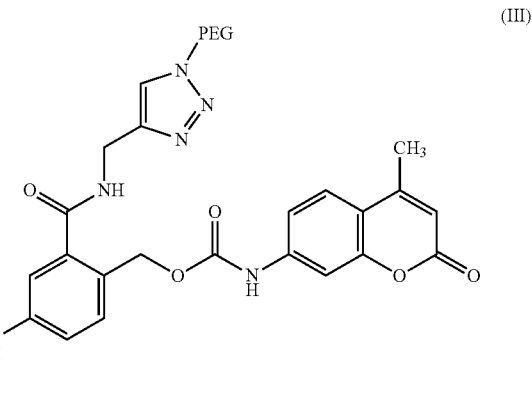

-continued
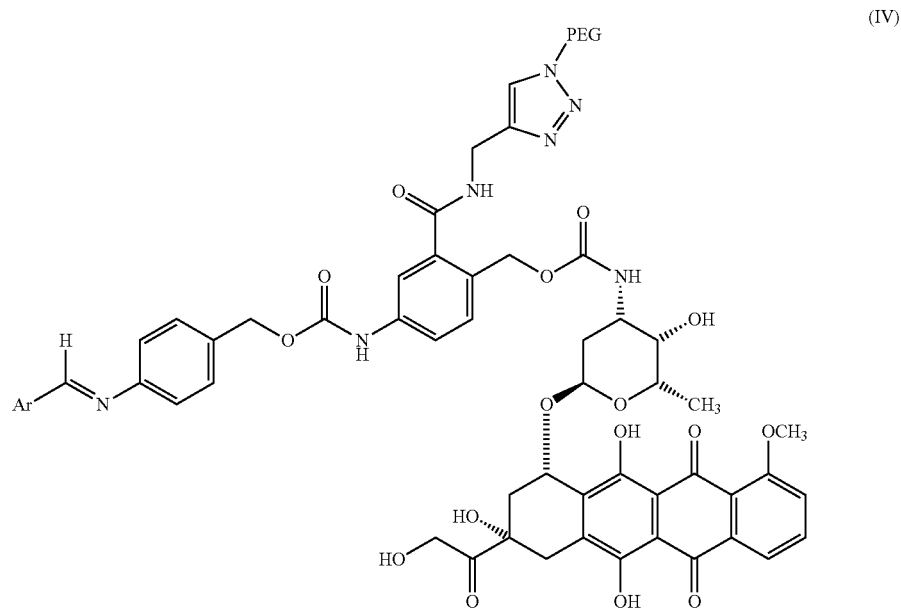
(IV)
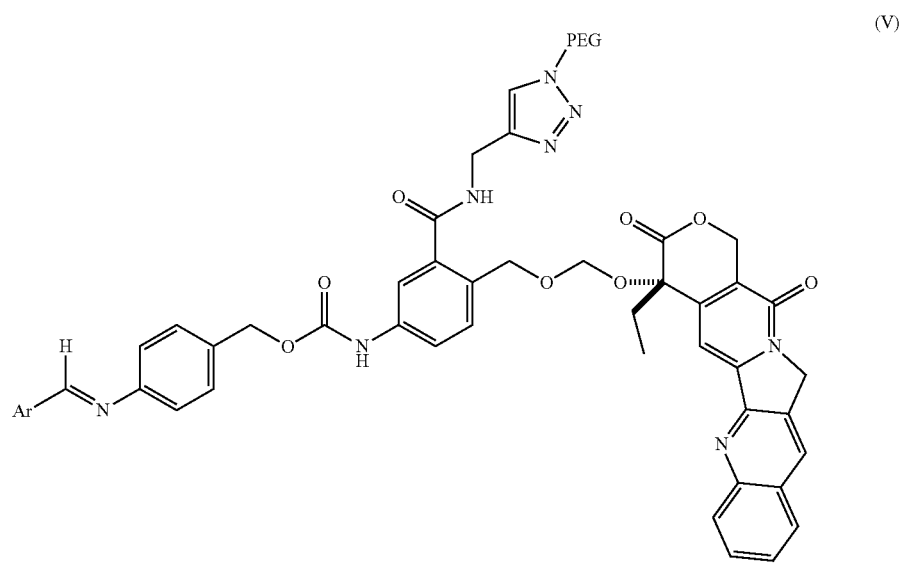
(V)

-continued

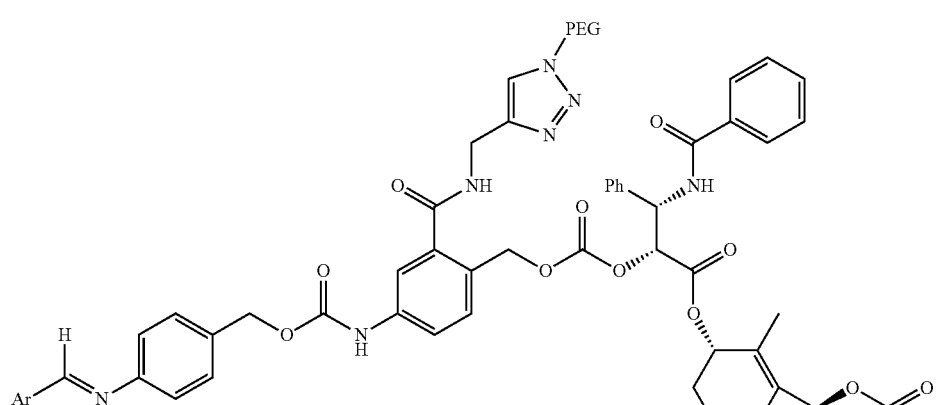

(VI)

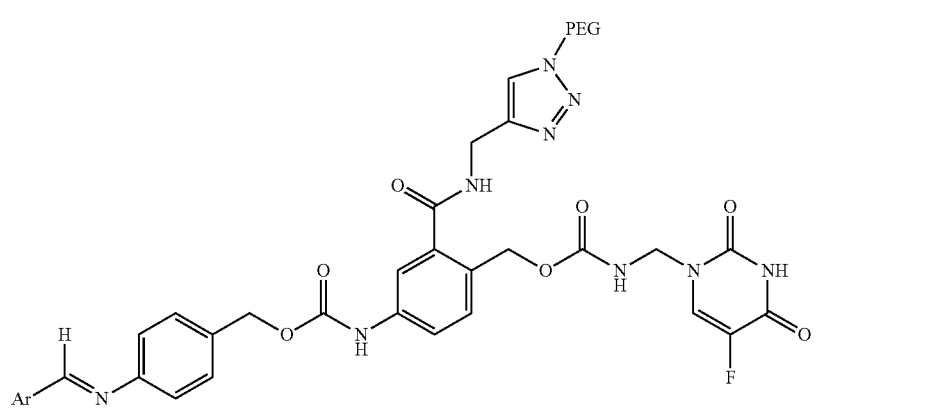

(VII)

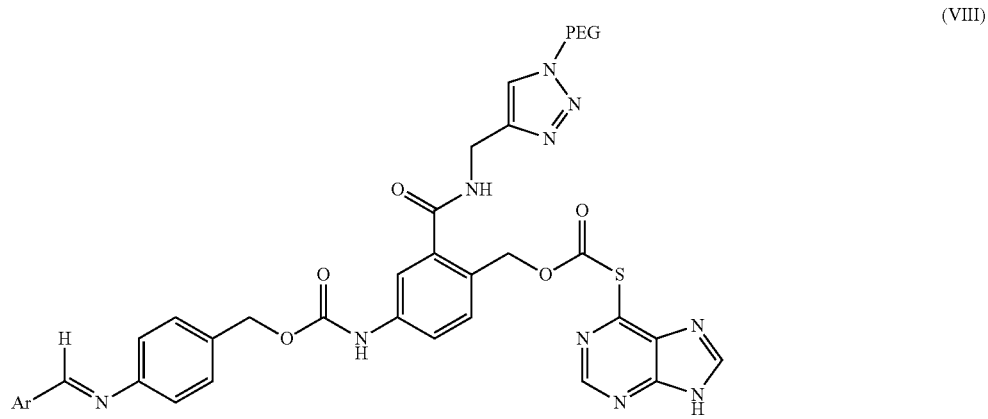

(VIII)

In the above compounds (III) to (VIII), n is 1 and the carrier group C is bound at the position $R_7$ via a linker group. Moreover, the effector moieties include 7-amino-4-methylcoumarin (formula (III)), doxorubicin (formula (IV)), camptothecin (formula (V)), paclitaxel (formula (VI)), 5-fluorouracil (formula (VII)) and 6-mercaptopurine (formula (VIII)).

The above compound of the formula (III) can be synthesized by the reaction scheme shown in FIG. 5. Moreover, the compounds of the formulas (IV) and (VIII) can be synthesized by the reaction scheme shown in FIG. 6, and the compound of formula (V) can be synthesized by the reaction scheme shown in FIG. 7. By similar methods, also the above compounds of formulas (VI) and (VII) can be synthesized.

As can be seen from the above reaction schemes, the compound of the present invention containing a carrier group at the position $R_7$ can generally be synthesized by a reaction sequence using the following building block (X) as a starting material:

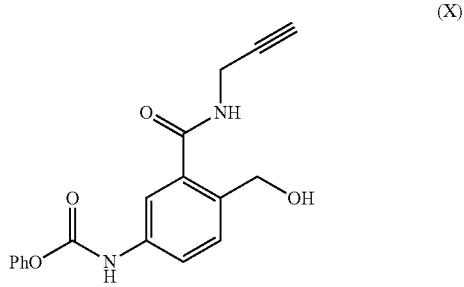 [SMILES: C#CCNC(=O)c1cc(NC(=O)Oc2ccccc2)ccc1CO]
(X)

Starting from the above building block (X), an azide-functionalized carrier can be coupled to the ethynyl group of building block (X) via e.g. a copper-catalyzed Huisgen cycloaddition. The aryl imine can be attached at the position of the blocked isocyanate (phenyl carbamate) via its hydroxy functionality. Moreover, the moiety E comprising at least one effector group can be coupled via the benzylic hydroxyl group of the building block (X). The above building block (X) can be synthesized by the reaction scheme shown in FIG. 8.

Moreover, the present invention relates to the use of a unit of the following structure

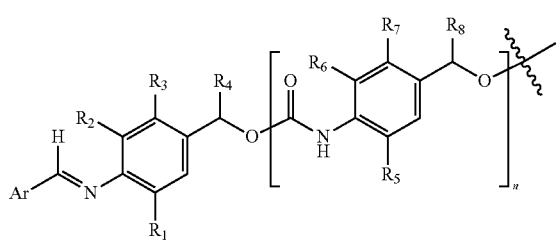

as a trigger group which can be cleaved pH-dependently, in the above-defined compound, wherein n, Ar and $R_1$ to $R_8$ are as defined above.

In particular, as explained above, the aryl imine unit contained in the compound of the present invention is a suitable trigger group which can be cleaved pH-dependently. Upon hydrolysis of the imine bond, the linker group(s) disassemble(s) and release(s) the moiety E comprising at least one effector unit.

The present invention further relates to a process of cleaving the imine bond in the above compound of the present invention, wherein the imine bond is cleaved upon a change in the pH value. In a preferred embodiment, the process comprises decreasing the pH value from a range of about 7.0 to 7.8 to a range of about 6.5 to 3.5. It is particularly preferred that the pH value is decreased from a value of about 7.0 to 7.4 to a range of about 4.5 to 5.5. In another preferred embodiment, the pH value is decreased by about 0.5 to 1.0 pH units, whereby the imine bond of the compound of the present invention is hydrolyzed. Preferably, the pH value is decreased upon endosomal uptake of the compound of the present invention into tumor cells by a ATP-dependent proton pump, or during the subsequent conversion into primary or secondary lysosomes.

Another aspect of the present invention relates to a pharmaceutical composition, comprising the compound as defined above, and optionally a pharmaceutically acceptable carrier and/or a pharmaceutically acceptable adjuvent and/or a diluent.

The pharmaceutical composition may for example contain solvents and diluents such as sodium chloride solution or a solution containing any pharmaceutically acceptable buffer. Moreover, the pharmaceutical composition of the present invention may be in any form suitable for administration to a patient, for example in an injectable form, as a tablette or a capsule, or as a composition for inhalation.

According to a specific embodiment, the above-defined pharmaceutical composition is for treatment of a disease selected from the group consisting of cancer, autoimmune diseases, acute or chronic inflammatory diseases, and diseases caused by viruses and/or microorganisms.

Another aspect of the present invention relates to the use of the compound as defined above in the manufacturing of a pharmaceutical composition for treating or diagnosing a patient suffering from a disease selected from the group consisting of cancer, autoimmune diseases, acute or chronic inflammatory diseases, and diseases caused by viruses and/or microorganisms.

According to a further specific embodiment, the above-defined pharmaceutical composition is for the treatment of cancer.

According to another embodiment of the present invention, the compound as defined above may be comprised in a kit, which may further contain one or more adjuvants, such as a buffer or a pharmaceutically acceptable carrier.

The Figures show:

According to the present invention, a compound is provided which comprises an acid-labile trigger group and which is suitably used as a prodrug. In particular, the imine bond of the compound is located at an exposed position and is therefore readily hydrolyzable. Moreover, due to the presence of one (when n is 0) or two (when n is 1) linker group(s), the disassembling reactions of the linkers leading to a release of the effector units are basically independent from the chemical nature of the effector units. Accordingly, it is possible to provide a specific and selective activation of the prodrug for a wide range of possible effector units. Moreover, the compounds of the present invention can be easily synthesized, since a general synthetic concept is available.

Moreover, the compound of the present invention has a high stability in the infusion solution, in the bloodstream and in the tissue fluid of healthy tissues, and is cleaved effectively and selectively in tumor tissues after take-up by a tumor cell, and can be used in combination with a great variety of drugs, without the need of the presence of a carbonyl functionality or an acyl hydrazide group in the drug.

The present invention is illustrated in the following example without any limitation thereto.

EXAMPLES

Figure 1A:
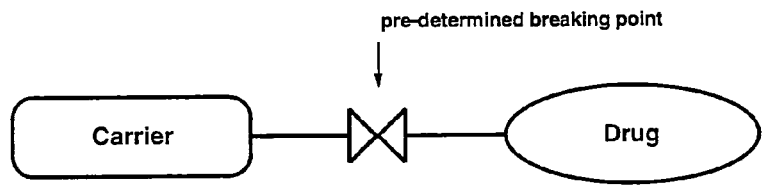
FIG. 1 shows a representation of the prodrug concept.
Figure 1B:
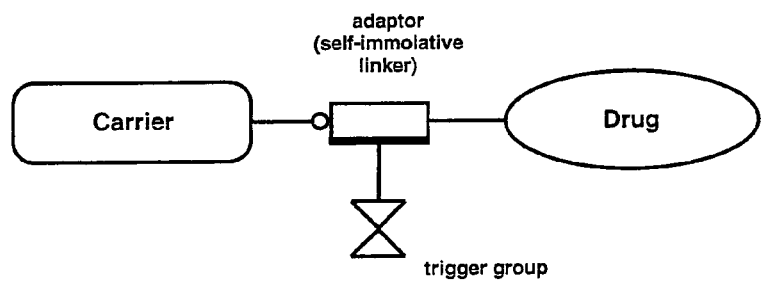
Figure 2:
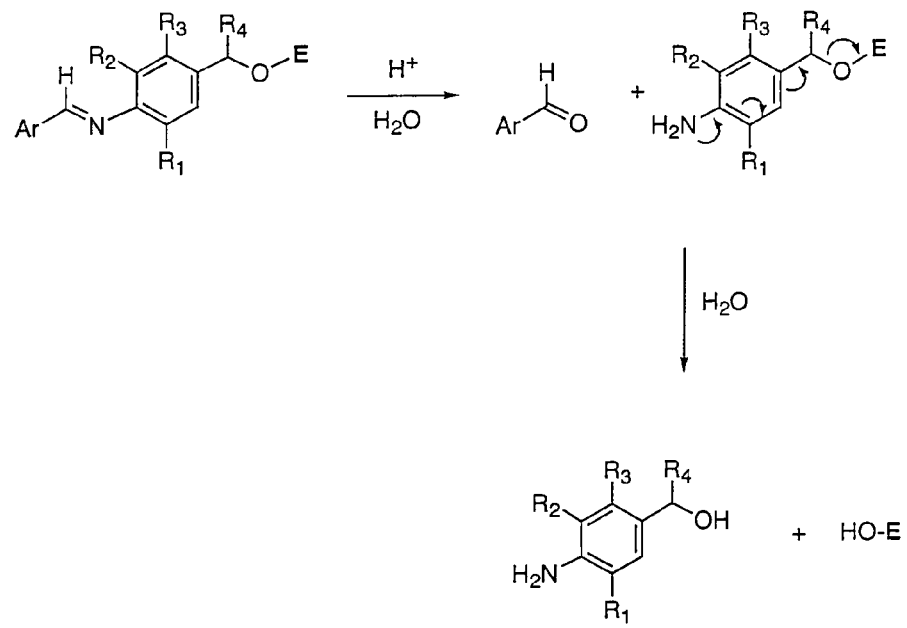
FIG. 2 shows 1,6-benzyl elimination reactions of the compound of the present invention.
Figure 3:
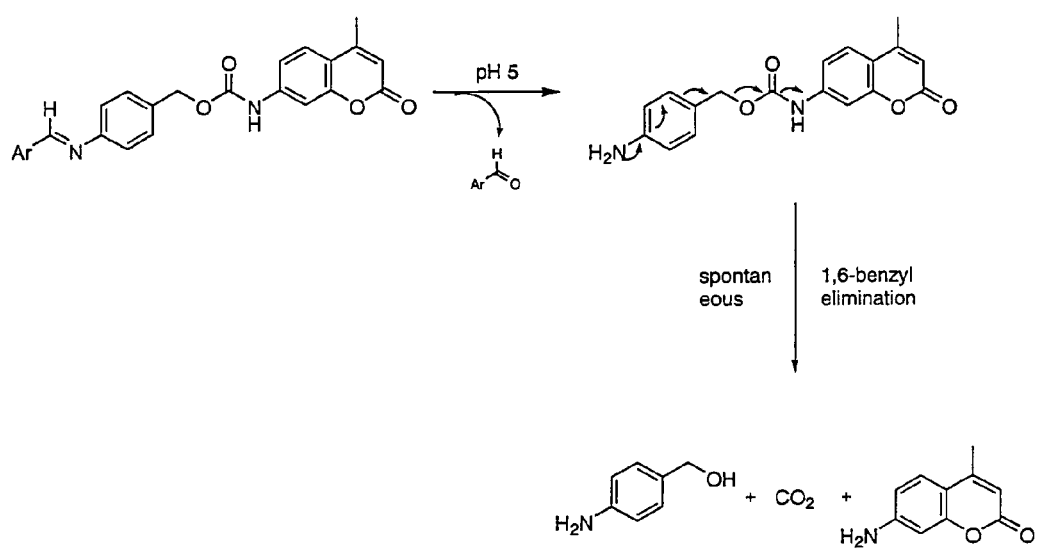
FIG. 3 shows the mechanism of cleavage of AMC-containing model compounds at acidic pH.
Figure 4:
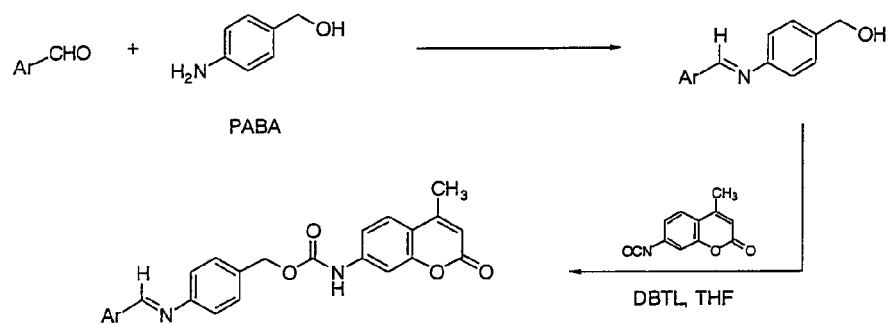
FIG. 4 shows the synthesis of the compound of formula (IX).
Figure 5:
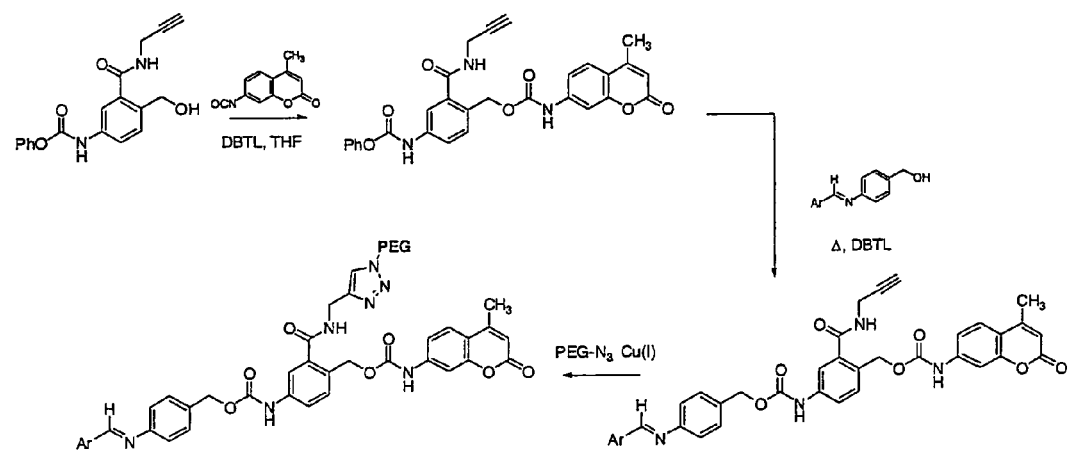
FIG. 5 shows the synthesis of the compound of formula (III).
Figure 6:
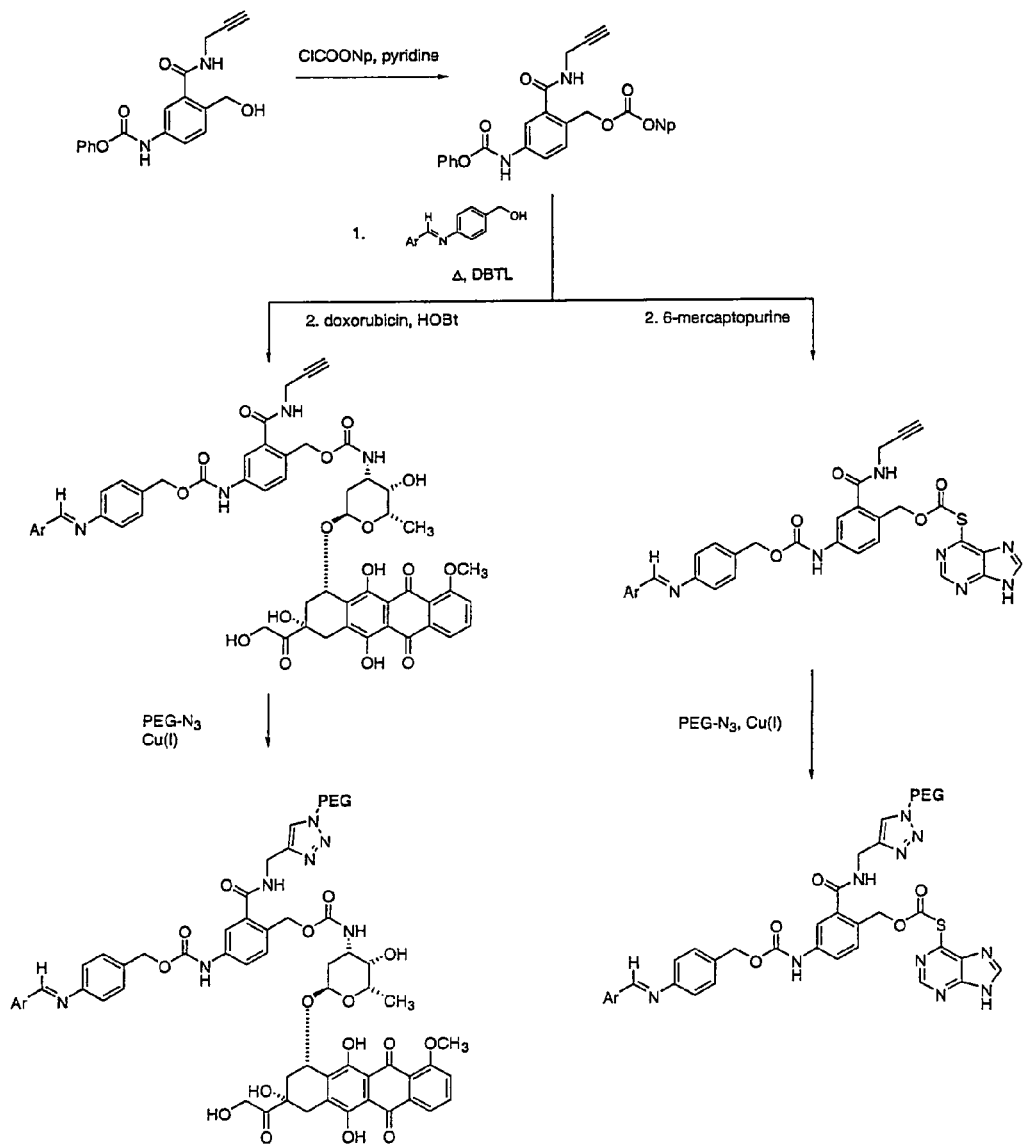
FIG. 6 shows the synthesis of the compounds of formulas (IV) and (VIII).
Figure 7:
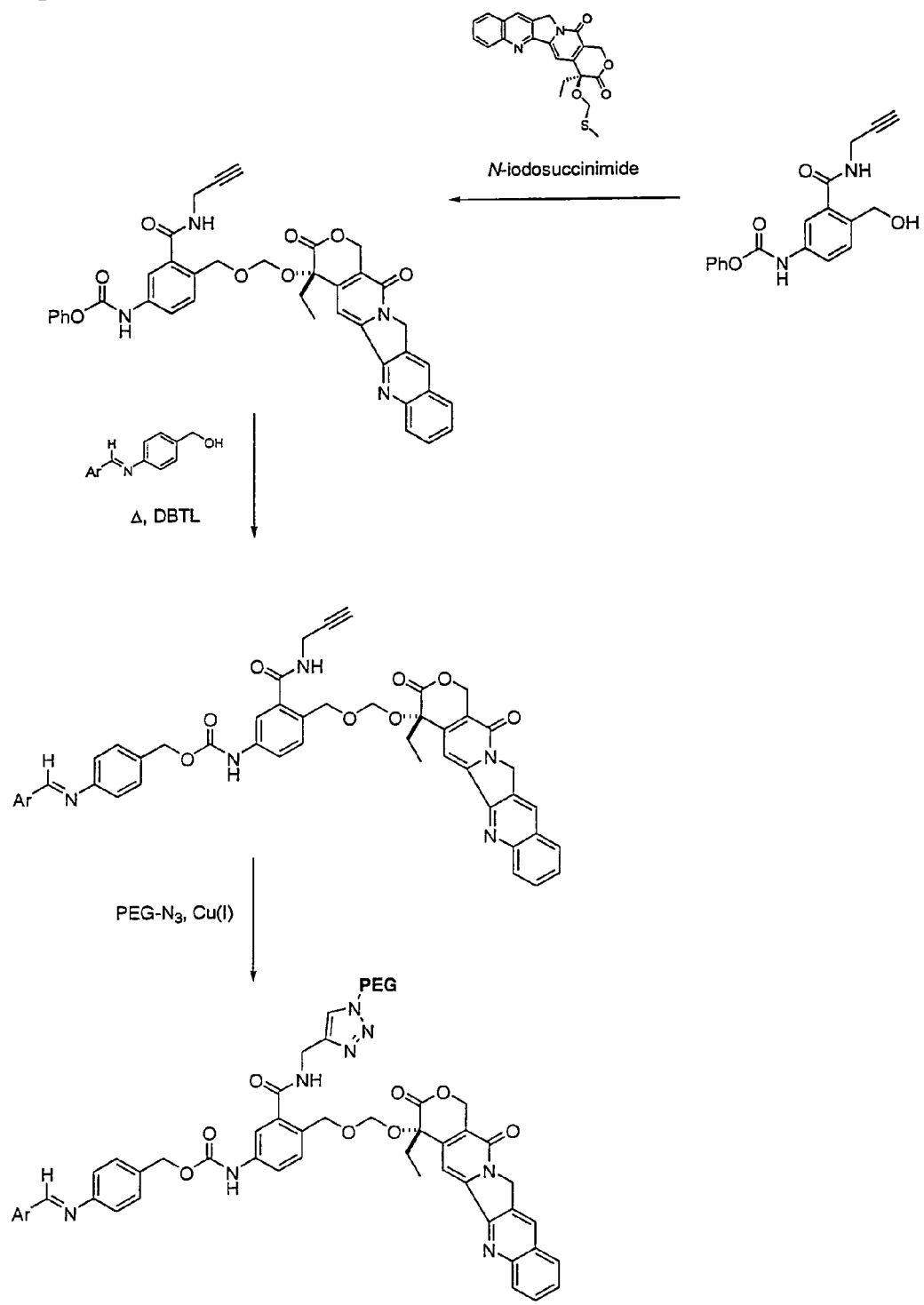
FIG. 7 shows the synthesis of the compound of formula (V).
Figure 8:
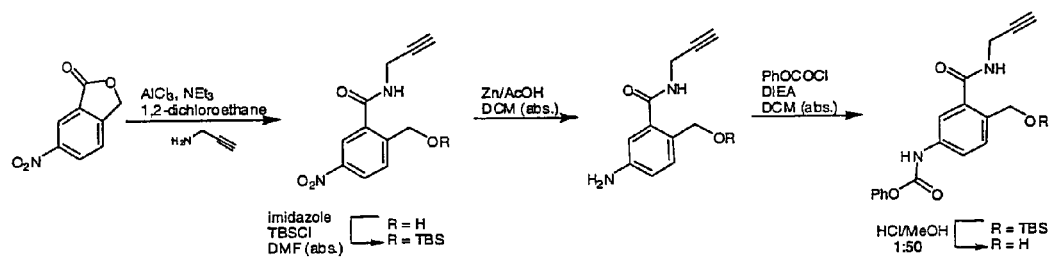
FIG. 8 shows the synthesis of the compound of formula (X).

The synthesis of the model compounds has been performed in two steps as shown in FIG. 4.

General Procedure for the Preparation of 4-(benzylideneamino)benzyl alcohols

The respective benzaldehyde derivative (4.86 mmol) and 5 μL (90 μmol) acetic acid are added to a stirred suspension of 200 mg (1.62 mmol) 4-aminobenzyl alcohol in 20 mL benzene. The mixture is heated to reflux for 17 h, and the formed water is removed using a Dean-Stark apparatus. After cooling down to room temperature, the solvent is removed under reduced pressure, and the product is crystallized from a mixture of n-hexane and ethyl acetate at −20° C.

4-(Benzylideneamino)benzyl alcohol (1). Pure product is obtained as a yellow solid in a yield of 252 mg (77%): $^1$H-NMR (400.1 MHz, DMSO-$d_6$): δ=4.52 (d, J=5.6 Hz, 2 H, $CH_2$), 5.21 (t, J=5.6 Hz, 1 H, OH), 7.24-7.26 (m, 2 H, Ar—H), 7.36-7.38 (m, 2 H, Ar—H), 7.53-7.54 (m, 3 H, Ar—H), 7.93-7.95 (m, 2 H, Ar—H), 8.64 (s, 1 H, C(N)H); $^{13}$C-NMR (100.6 MHz, DMSO-$d_6$): δ=63.0 ($CH_2$), 121.2, 127.8, 129.0, 129.2, 131.8, 136.5, 140.9, 150.4, 160.5 (Ar—C, C(N)H); APCI-MS (5 uA, MeOH): m/z (%)=212 (100) [$M^+$+$H^+$].

4-(2,3,5,6-Tetrafluorobenzylideneamino)benzyl alcohol (2). Pure product is obtained as a yellow solid in a yield of 345 mg (75%): $^1$H-NMR (400.1 MHz, DMSO-$d_6$): δ=4.53 (d, J=5.7 Hz, 2 H, $CH_2$), 5.28 (t, J=5.7 Hz, 1 H, OH), 7.28-7.31 (m, 2 H, Ar—H), 7.39-7.41 (m, 2 H, Ar—H), 8.03-8.12 (m, 1 H, Ar—H), 8.69 (s, 1 H, C(N)H); $^{13}$C-NMR (100.6 MHz, DMSO-$d_6$): δ=62.4 ($CH_2$), 109.3 (dd, $J_1$=19.6 Hz, $J_2$=19.6 Hz, Ar—C), 116.3 (dd, $J_1$=11.1 Hz, $J_2$=11.1 Hz, Ar—C), 121.2, 127.8, 142.3 (Ar—C), 145.2 (m, CF), 145.8 (m, CF), 149.7, 149.8 (Ar—C, C(N)H); ESI-MS (5 kV, ACN): m/z (%)=284 (100) [$M^+$+$H^+$].

4-(Perfluorobenzylideneamino)benzyl alcohol (3). Pure product is obtained as a colorless solid in a yield of 408 mg (84%): $^1$H-NMR (400.1 MHz, DMSO-$d_6$): δ=4.53 (d, J=5.7 Hz, 2 H, $CH_2$), 5.25 (t, J=5.7 Hz, 1 H, OH), 7.28-7.30 (m, 2 H, Ar—H), 7.38-7.40 (m, 2 H, Ar—H), 8.66 (s, 1 H, C(N)H): $^{13}$C-NMR (100.6 MHz, DMSO-$d_6$): δ=62.8 ($CH_2$), 111.6 (ddd, $J_1$=11.3 Hz, $J_2$=7.1 Hz, $J_3$=3.9 Hz, Ar—C), 121.2, 127.7 (Ar—C), 137.7 (m, CF), 142.3 (Ar—C), 142.1 (m, CF), 145.8 (m, CF), 149.0, 149.7 (Ar—C, C(N)H); ESI-MS (5 kV, ACN): m/z (%)=302 (100) [$M^+$+$H^+$].

General Procedure for the Preparation of 4-(benzylideneamino)benzyl 4-methylcoumarin-7-ylcarbamates Molecular sieve 4 Å (20 mg), 4-(benzylideneamino)benzyl alcohol (497 μmol) and 25 μL (2.5 μmol) of a 0.1 M solution of dibutyltin dilaurate in toluene are added to a stirred solution of 100 mg (497 μmol) 7-isocyanato-4-methylcoumarin in 8 mL THF. After 0.5 h stirring at room temperature, the resulting solid is carefully filtered off and washed with 15 mL n-hexane.

4-(Benzylideneamino)benzyl 4-methylcoumarin-7-ylcarbamate (4). After recrystallization from dichloromethane, pure product is obtained as a white solid in a yield of 135 mg (66%): $^1$H-NMR (400.1 MHz, DMSO-$d_6$): δ=2.40 (s, 3 H, $CCH_3$), 5.23 (s, 2 H, $CH_2$), 6.22 (s, 1 H, $CH_3CCH$), 7.29-7.31 (m, 2 H, Ar—H), 7.43-7.57 (m, 7 H, Ar—H), 7.68-7.71 (m, 1 H, Ar—H), 7.93-7.96 (m, 2 H, Ar—H), 8.63 (s, 1 H, C(N)H), 10.18 (bs, 1 H, NH); $^{13}$C-NMR (100.6 MHz, DMSO-$d_6$): δ=18.3 ($CH_3$), 66.4 ($CH_2$), 105.1, 112.4, 114.8, 114.9 ($CH_3C$ CH, Ar—C), 121.4, 126.3, 129.1, 129.2, 129.7, 131.9, 134.3, 136.4, 143.2, 151.9 (Ar—C), 153.5, 153.6, 154.3, 160.4, 161.3 (C(O)NH, $CCH_3$, Ar—C, C(N)H, C(O)CH); APCI-MS (5 uA, MeOH): m/z (%)=413 (100) [$M^+$+$H^+$].

4-(2,3,5,6-Tetrafluorobenzylideneamino)benzyl 4-methylcoumarin-7-ylcarbamate (5). Pure product is obtained as a white solid in a yield of 197 mg (82%): $^1$H-NMR (400.1 MHz, DMSO-$d_6$): δ=2.39 (s, 3 H, $CCH_3$), 5.24 (s, 2 H, $CH_2$), 6.24 (s, 1 H, $CH_3CCH$), 7.34-7.37 (m, 2 H, Ar—H), 7.41-7.44 (m, 1 H, Ar—H), 7.53-7.70 (m, 3 H, Ar—H), 7.69-7.71 (m, 1 H, Ar—H), 8.08-8.14 (m, 1 H, CFCH), 8.72 (s, 1 H, C(N)H), 10.32 (bs, 1 H, NH); $^{13}$C-NMR (100.6 MHz, DMSO-$d_6$): δ=18.4 ($CCH_3$), 66.2 ($CH_2$), 109.5 (dd, $J_1$=23.1 Hz, $J_2$=23.1 Hz, CFCCF), 104.8, 112.3, 114.7, 114.8 ($CH_3CCH$, Ar—C), 116.1 (dd, $J_1$=10.8 Hz, $J_2$=10.8 Hz, CFCCF), 121.6, 126.5, 129.8, 135.6, 143.1 (Ar—C), 145.5 (m, CF), 146.0 (m, CF), 150.8, 151.1, 153.5, 153.6, 154.2, 160.4 (Ar—C, C(O)NH, $CCH_3$, C(N)H, C(O)CH); ESI-MS (5 kV, ACN): m/z (%)=485 (100) [$M^+$+$H^+$].

4-(Perfluorobenzylideneamino)benzyl 4-methylcoumarin-7-ylcarbamate (6).

Pure product is obtained as a yellow solid in a yield of 218 mg (87%): $^1$H-NMR (400.1 MHz, DMSO-$d_6$): δ=2.38 (s, 3 H, $CCH_3$), 5.23 (s, 2 H, $CH_2$), 6.24 (s, 1 H, $CH_3CCH$), 7.34-7.36 (m, 2 H, Ar—H), 7.40-7.41 (m, 1 H, Ar—H), 7.43-7.56 (m, 3 H, Ar—H), 7.69-7.71 (m, 1 H, Ar—H), 8.66 (s, 1 H, C(N)H), 10.32 (bs, 1 H, NH); $^{13}$C-NMR (100.6 MHz, DMSO-$d_6$): δ=18.4 ($CCH_3$), 66.2 ($CH_2$), 111.5 (m, CFCCF), 104.9, 112.4, 114.7, 114.8 ($CH_3CCH$, Ar—C), 121.6, 126.5, 129.8, 135.6 (Ar—C), 137.7 (m, CF), 139.8 (m, CF), 143.1 (Ar—C), 146.7 (m, CF), 150.1, 151.0, 153.5, 153.6, 154.2, 160.4 (Ar—C, C(O)NH, $CCH_3$, C(N)H, C(O)CH); APCI-MS (5 uA, MeOH): m/z (%)=503 (100) [$M^+$+$H^+$].

Determination of half-lives for the imine hydrolysis in model compounds
Measurement Conditions:
200 μL solution per well;
Wavelength: $\lambda_{ex}$=390 nm, $\lambda_{em}$=460 nm;
Temperature: 37° C.

TABLE

Half-lives of imine hydrolysis.

| Compound | Aldehyde | $t_{1/2}$ pH 5.0* [min] | $t_{1/2}$ pH 7.4** [h] |
|---|---|---|---|
| 4 | benzaldehyde | 34 | 8 |
| 5 | 2,3,5,6-tetrafluorobenzaldehyde | 34 | 89 |
| 6 | pentafluorobenzaldehyde | 173 | 365 |

*Acetate buffer, 20 mM;
**Phosphate buffer, 20 mM

The data show that the introduction of fluorine substituents in the benzaldehyde system leads to a dramatic increase in stability at neutral pH whereas the rate of cleavage under acidic conditions remains less affected.

The invention claimed is:

1. A compound of the following general formula (I):

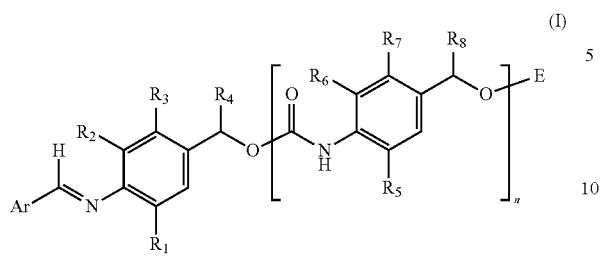

wherein
Ar is a phenyl group having one or more hydrogens substituted with a substituent independently selected from the group consisting of an $C_{1-6}$ alkyl group, a $C_{1-6}$ thioalkyl group, a $C_{3-7}$ cycloalkyl group which may contain one or more heteroatoms, an $C_{1-6}$ alkoxy group, a $C_{1-6}$ dialkylamine group, an $C_{1-6}$ alkoxycarbonyl group, a $C_{1-6}$ trialkylammonium group, a nitro group, a hydroxy group, a $C_{1-6}$ perfluoroalkyl group, fluorine, chlorine and bromine,
n is 0 or 1,
$R_1$, $R_2$, $R_5$ and $R_6$ are independently selected from hydrogen, a linear or branched $C_{1-8}$ alkyl group, a phenyl group, a naphthyl group, a biphenyl group or a vinyl benzene group, or a group C,
$R_3$, $R_4$, $R_7$ and $R_8$ are independently selected from hydrogen or a group C, with the proviso that not more than one of $R_1$ to $R_8$ is a group C,
E is a moiety comprising at least one cytostatic agent as an effector unit which is selected from the group consisting of N-nitrosoureas, the anthracyclines doxorubicin, daunorubicin, epirubicin, idarubicin, 2-(4-diacetoxybutyl)doxorubicin; the anthraquinones mitoxantrone and ametantrone; the alkylating agents chlorambucil, bendamustine, melphalan, and oxazaphosphorines; the antimetabolites 5-fluorouracil, 2'-deoxy-5-fluorouridine, cytarabine, cladhbine, fludarabine, pentostatine, gemcitabine, 6-thioguanine and 6-mercaptopurine; the folic acid antagonists methotrexate, raltitrexed, pemetrexed and plevitrexed, the taxanes paclitaxel and docetaxel; the camptothecins topotecan, irinotecan (CPT-11), SN-38, 10-hydroxycamptothecin, GG211, lurtotecan, 9-aminocamptothecin and camptothecin; the lignans etoposide and podophyllotoxin; the Vinca alkaloids vinblastine, vincristine, vindesine and vinorelbine; calicheamicins; maytansinoids; auristatins; epothilones; tubulysins, rapamycin, salinosporamide, combretastatin, bleomycin; dactinomycin; plicamycin; mitomycin C and cis-configured platinum(II) complexes, and
C is a carrier group selected from the group consisting of serum proteins, antibodies or antibody fragments, synthetic polymers, dendrimers, peptides, growth factors, receptor-binding ligands, polysaccharids, microparticles, nanoparticles and protein-binding moieties capable of binding to a carrier molecule,
wherein the carrier group may be bound to the phenyl ring or to the benzylic carbon atom directly or via a linker.

2. The compound according to claim 1, wherein Ar is selected from one of the following groups:

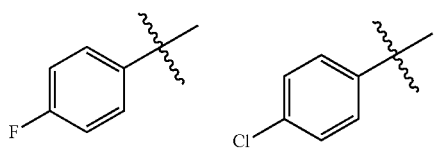

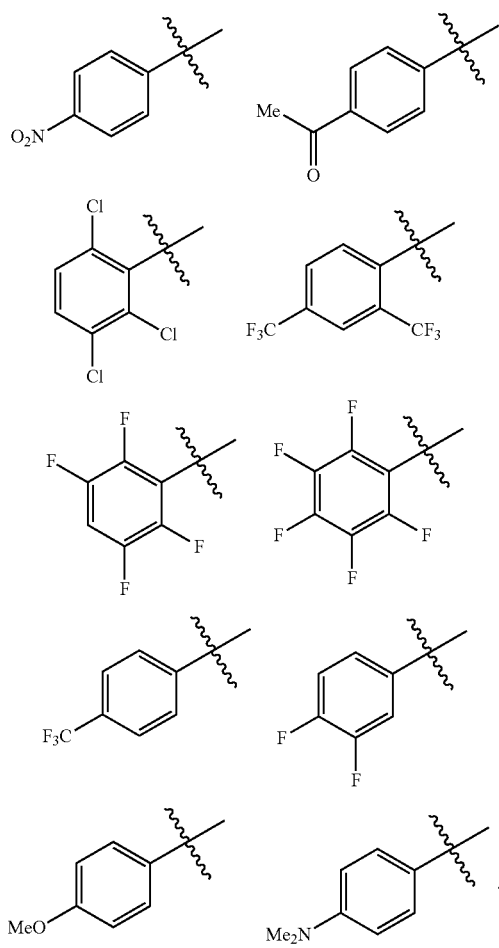

3. The compound according to claim 2, wherein Ar is selected from one of the following groups:

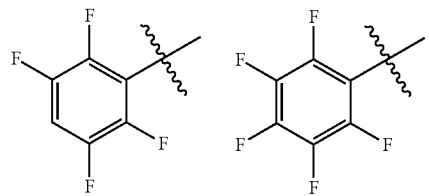

4. The compound according to claim 1, wherein the effector unit is bound via a —(O)O—, a —C(O)S—, a —C(O)NH—, a —CH$_2$O— or a —C(O)NH—CH$_2$N— group.

5. The compound according to claim 1, wherein one of $R_1$ to $R_8$ is a carrier group C which is a protein-binding moiety selected from the group consisting of a maleimide group, a halogenacetamide group, a halogenacetate group, a pyridylthio group, a vinylcarbonyl group, an aziridin group, a disulfide group, a substituted or unsubstituted acetylene group, and a hydroxysuccinimide ester group.

6. The compound according to claim 1, wherein one of $R_1$ to $R_8$ is a carrier group C which is a protein-binding moiety capable of in situ binding to cysteine-34 of serum albumin.

7. The compound according to claim 1, which has the following general formula (II):

(II)
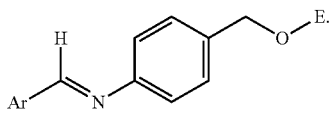

8. The compound according to claim 1, wherein one of $R_1$ to $R_8$ is a carrier group C which is a synthetic polymer selected from the group consisting of poly(ethylene glycol) (PEG), monomethoxy PEG (mPEG), polyglycerol (PG), poly(ethylene amine) (PEI) and N-(2-hydroxy)propylmethacrylamide (HPMA) copolymers.

9. The compound according to claim 8, wherein one of $R_2$, $R_3$, $R_4$, $R_6$, $R_7$ and $R_8$ is the carrier group C, which is bound to the phenyl ring via a linker having one of the following structures, wherein m is an integer from 0 to 5:

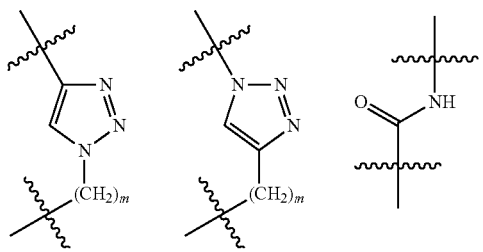

-continued

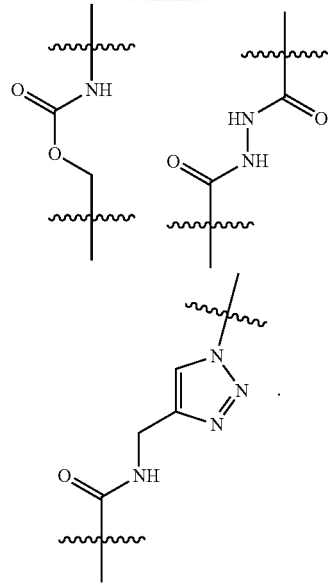

10. The compound according to claim 9, which has one of the following structures (III), (IV), (V), (VI), (VII) or (VIII), wherein PEG is poly(ethylene glycol) or monomethoxy poly(ethylene glycol):

(III)
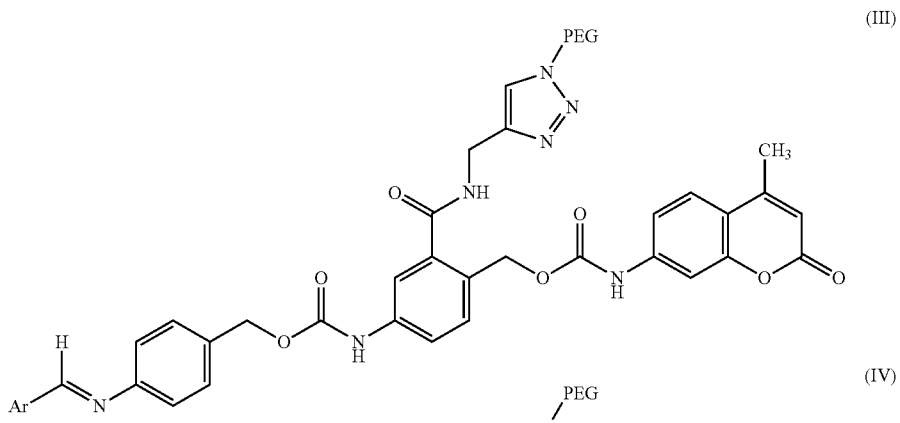

(IV)
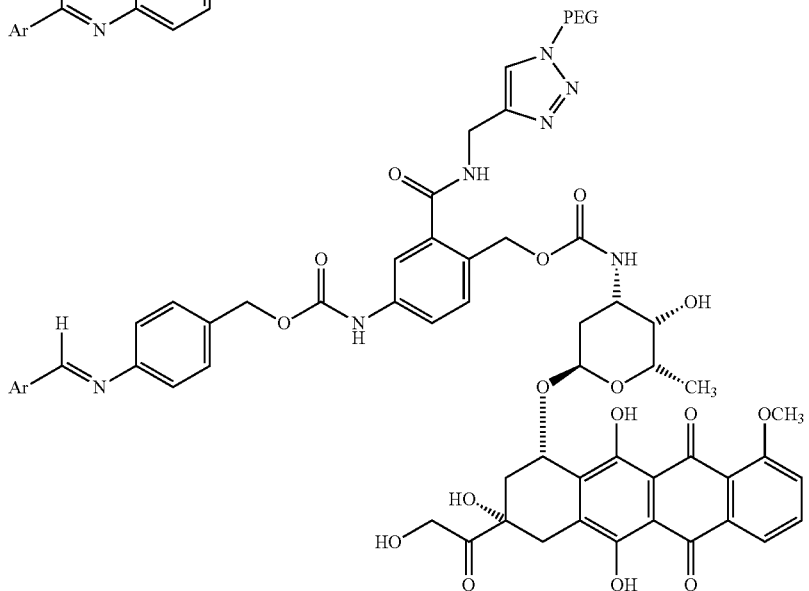

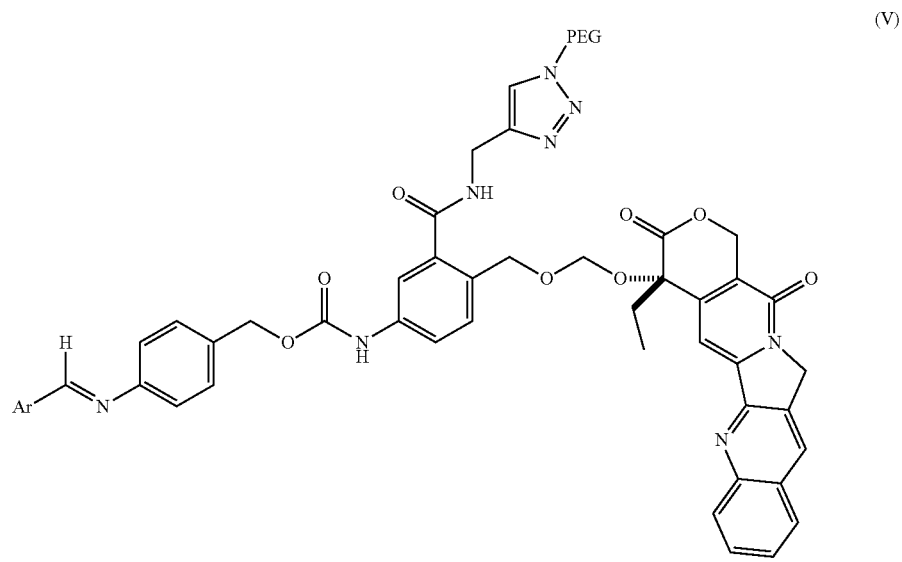
(V)
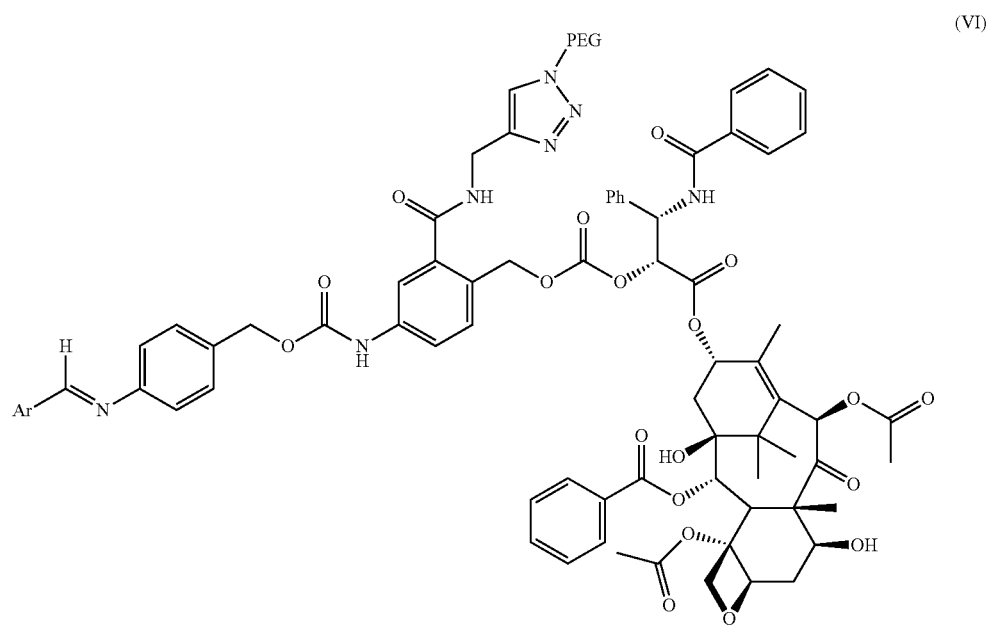
(VI)
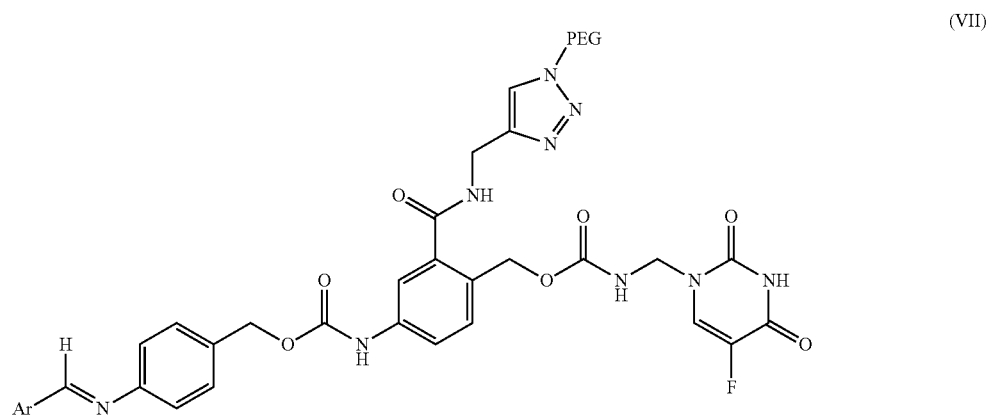
(VII)

-continued

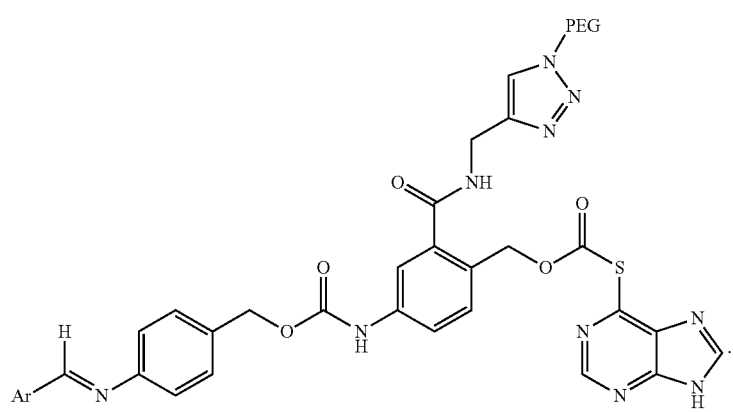

(VIII)

11. The compound according to claim 1, wherein the moiety E is a dendritic or linear system adapted to release one or more effector units upon cleavage of the imine bond in the compound of general formula (I).

12. A method for producing a compound of claim 1, said method comprising attaching to moiety E a unit of the following structure

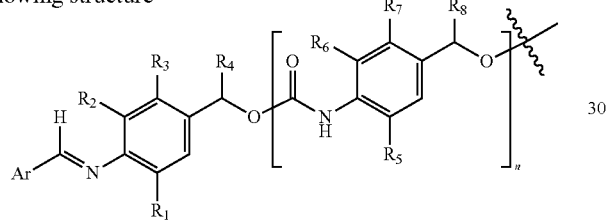

as a trigger group which can be cleaved pH-dependently, wherein E, n, Ar and $R_1$ to $R_8$ are as defined above.

13. A composition comprising the compound according to claim 1, and optionally a pharmaceutically acceptable carrier and/or a pharmaceutically acceptable adjuvant and/or a diluent.

\* \* \* \* \*